Dec. 16, 1941. W. I. JOHNSTON Plant Pat. 495
ROSE PLANT
Filed July 18, 1941
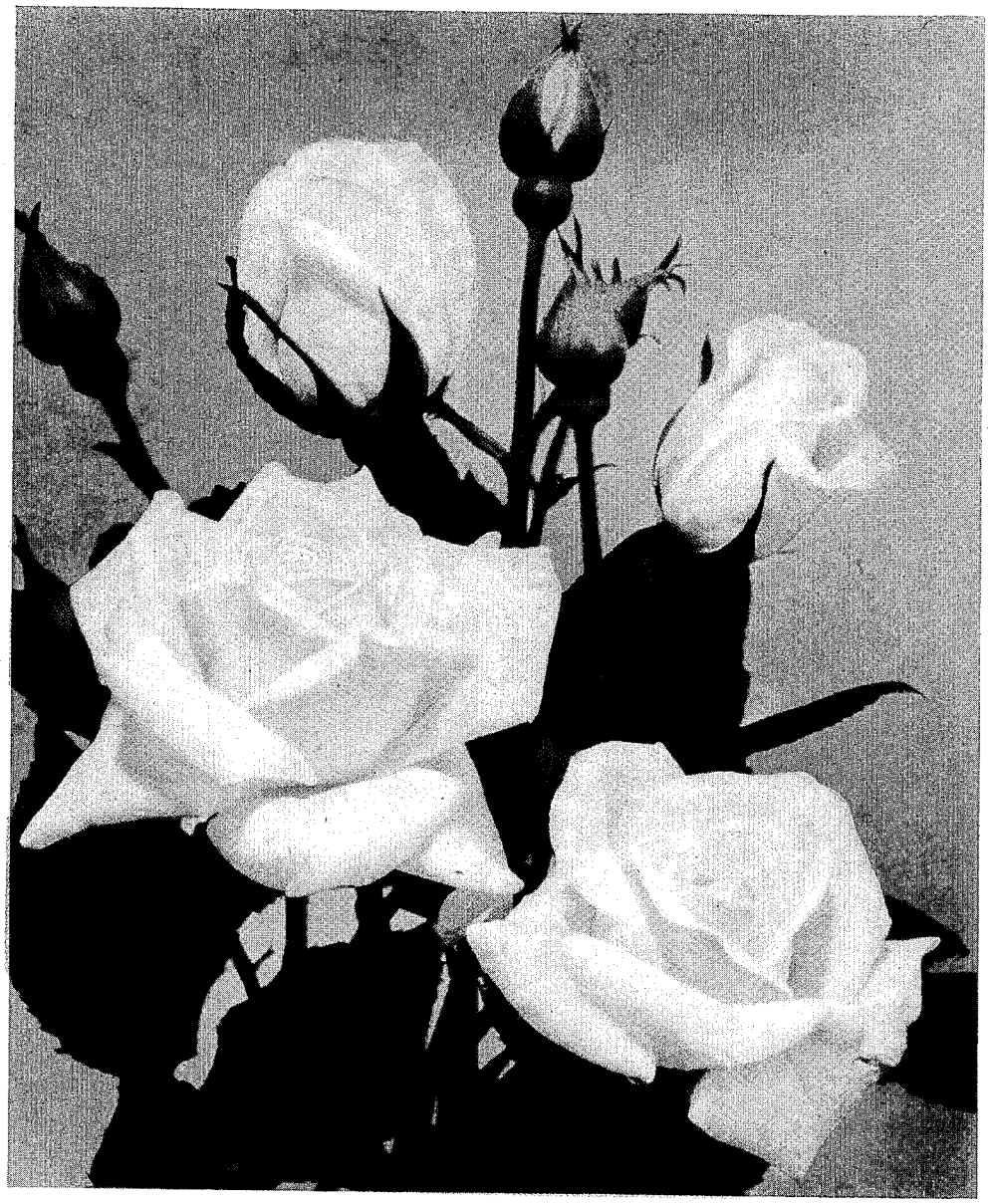
Inventor
W. I. Johnston
By Robert Cobb
Attorneys Patented Dec. 16, 1941

Plant Pat. 495

UNITED STATES PATENT OFFICE

495

ROSE PLANT

Walter Irwin Johnston, Portadown, Ireland, assignor to Jackson & Perkins Company, Newark, N. Y.

Application July 18, 1941, Serial No. 403,066

1 Claim. (Cl. 47—61)

The present invention relates to a new and distinct hybrid tea rose plant, a cross between "Portadown Glory" and an unknown seedling, resulting in a rose of a new yellow color among the yellow class. The uniformity of this color—Pinard Yellow, and its lack of fading even in the hottest sun places this new variety in a class by itself.

The green foliage and dark Victoria Lake color of the new foliage also lend attractiveness to this rose.

Other important novel characteristics to be noted are its symmetry of form, and continuity of blooming throughout the entire season.

The following is a detail description of the new variety, color terminology being in accord with Ridgway's Color Standard.

Parentage: Seedling.

*Seed parent.*—Unnamed seedling.

*Pollen parent.*—Portadown Glory.

Classification: Botanic and commercial—hybrid tea.

*Flower*

(Observations made in the field of Jackson & Perkins Company, Newark, New York, on October 4, 1940.)

Blooming Habit: Recurrent—continuous.

Bud:

*Size.*—Medium.

*Form.*—Ovoid. Is not affected by wet or hot weather.

*Color.*—When sepals first divide—Light Greenish Yellow, Plate 5. When petals begin to unfurl—Picric Yellow, Plate 4. When half blown: inside of petals—Strontian Yellow, Plate 16; reverse of petals—Citron Yellow, Plate 16.

*Sepals.*—Branched; "hood" above bud. Curl back when petals unfurl. Color: upper side—Light Cress Green, Plate 31; under side—Absinthe Green, Plate 31.

*Calyx.* — *Shape*—apple. *Size*—broad. *Aspect*—smooth. *Color*—Light Cress Green, Plate 31.

*Peduncle.* — *Length* — medium. *Aspect* — smooth. *Color*—Rainette Green, Plate 31, overlaid with Cinnamon, Plate 29. *Strength*—Erect; heavy.

*Opening.*—Bud opens well. Is not affected by adverse conditions.

Bloom:

*Size.*—Large.

*Quantity of bloom.*—Very many. Average size when fully expanded—4½".

*Borne.*—Singly and several together.

*Stems.*—Medium length; strong.

*Form.*—*When first open*—high center. *Permanence*—retains its form to the end.

*Petalage.*—Double (full but open center). Number of petals under normal conditions—27.

*Color.*—Center of flower—Empire Yellow, Plate 4. Outer petals—Pinard Yellow, Plate 4, darkening to Empire Yellow at base, Plate 4. Base of petals (aiglet)—Lemon Chrome, Plate 4. Inside of petals—Empire Yellow, Plate 4. Reverse of petals—Pinard Yellow, Plate 4, darkening to Empire Yellow, at base, Plate 4. General tonality from a distance—Empire Yellow, Plate 4.

*Discoloration.*—General tonality at end of first day—Empire Yellow, Plate 4. Second day—Pinard Yellow, Plate 4. Third day—Pinard Yellow, Plate 4.

Petals:

*Texture.*—Leathery. Is not affected by wet or hot weather.

*Appearance.* — Inside — satin. Outside — shiny.

*Form.*—Oval.

*Arrangement.*—Imbricated (regularly arranged shingle-like). *Petaloids in center*—few; small.

*Peristence.*—Drop off cleanly.

*Fragrance.*—Slight. *Nature*—fruity (Russet apple).

*Lasting quality.*—On the plant and as cut flower—long.

Genital Organs:

*Stamens, anthers.*—Medium size; many. *Color*—Empire Yellow, Plate 4. *Arrangement*—regular around styles.

*Stamens, filaments (threads).*—Long. *Color*—Lemon Yellow, Plate 4.

*Pollen.*—Martius Yellow, Plate 4.

*Styles.*—Bunched, even; medium length; thin.

*Stigmas.*—Pinard Yellow, Plate 4.

*Ovaries.*—All enclosed in calyx.

*Plant*

Form: Bush.
Growth: Medium; upright.
Foliage: 5–7 *leaflets.*
*Size.*—Medium.
*Quantity.*—Normal.
*Color.*—*New foliage:* upper side—Victoria Lake, Plate 1, with the tip of Parrot Green, Plate 6; under side—Oxblood Red, Plate 1, with the tip of Oil Green, Plate 5. *Old foliage:* upper side—Yew Green, Plate 31; under side—Rainette Green, Plate 31, with slight veining of Oxblood Red, Plate 1.
*Shape.*—Oval.
*Texture.*—Upper side—glossy. Under side—rough. *Ribs and veins*—ordinary.
*Edge.*—Serrated (saw-toothed).
*Serration.*—Single; sharp.
*Rachis.*—*Color*—yellowish. Under side—smooth.
*Stipules.*—Medium length; slightly bearded.
*Disease resistance.*—Resistant.

Wood:
*New wood.*—*Color*—Mignonette Green, Plate 31. *Bark*—Smooth.
*Old Wood.*—*Color*—Cress Green, Plate 31. *Bark*—Smooth.

Thorns (thorns are divided into thorns, prickles, and short needles):
*Thorns.*—On main stalks from base and on laterals from stalk—few. *Form*—flat base; medium length; straight. *Color when young*—Sayal Brown, Plate 29. *Position.* irregular.
*Prickles.*—On main stalks and on laterals—few. *Color*—Sayal Brown, Plate 29.

I claim:

A new and distinct variety of hybrid tea rose plant characterized as to novelty by the new unfading Yellow color of its flowers, symmetry of form, continuity of blooming, and attractive green foliage, substantially as shown and described.

WALTER IRWIN JOHNSTON.